United States Patent [19]

Lüder et al.

[11] Patent Number: 4,482,882
[45] Date of Patent: Nov. 13, 1984

[54] MOISTURE SENSOR WITH VALVE METAL COMPOSITION ELECTRODES

[75] Inventors: Ernst Lüder, Stuttgart; Traugott Kallfass, Grossbottwar; Christian Borgwardt, Stuttgart, all of Fed. Rep. of Germany

[73] Assignee: Endress u. Hauser GmbH u. Co., Fed. Rep. of Germany

[21] Appl. No.: 445,656

[22] Filed: Nov. 30, 1982

[30] Foreign Application Priority Data

Dec. 28, 1981 [DE] Fed. Rep. of Germany ....... 3151630

[51] Int. Cl.$^3$ ............................................. H01L 7/00
[52] U.S. Cl. ..................................... 338/34; 338/308; 338/309; 73/335; 73/336.5
[58] Field of Search .......................... 38/35, 34, 308; 73/336.5, 335; 324/65 R, 65 P; 338/35, 34, 308, 309, 307

[56] References Cited

U.S. PATENT DOCUMENTS

| | | | |
|---|---|---|---|
| 4,217,623 | 8/1980 | Nishono et al. | 73/336.5 X |
| 4,358,748 | 11/1982 | Gruner et al. | 338/308 X |
| 4,393,434 | 7/1983 | Imai et al. | 73/336.5 X |
| 4,433,319 | 2/1984 | Lüder et al. | 338/34 |

FOREIGN PATENT DOCUMENTS

| | | | |
|---|---|---|---|
| 2938434 | 11/1980 | Fed. Rep. of Germany | 73/336.5 |
| 6146222 | 11/1981 | Japan | 73/336.5 |
| 1577724 | 10/1980 | United Kingdom | 73/336.5 |

Primary Examiner—C. L. Albritton
Assistant Examiner—C. N. Sears
Attorney, Agent, or Firm—Gerald J. Ferguson, Jr.; Joseph J. Baker

[57] ABSTRACT

A moisture sensor comprises a moisture-sensitive layer formed from the oxide of highly resistive porous low density tantalum on a moisture-insensitive substrate. Between the substrate and the moisture-sensitive tantalum oxide layer there is a base electrode of an anodically oxidizable metal, preferably tantalum, of a density higher than the density of the low density tantalum from which the tantalum oxide layer is formed. A covering electrode partially covering the tantalum oxide layer has windows through which the water vapor containing medium can penetrate into the moisture-sensitive tantalum oxide layer. The inactive regions of the tantalum oxide layer disposed below the windows are removed to increase the rate of response.

12 Claims, 17 Drawing Figures

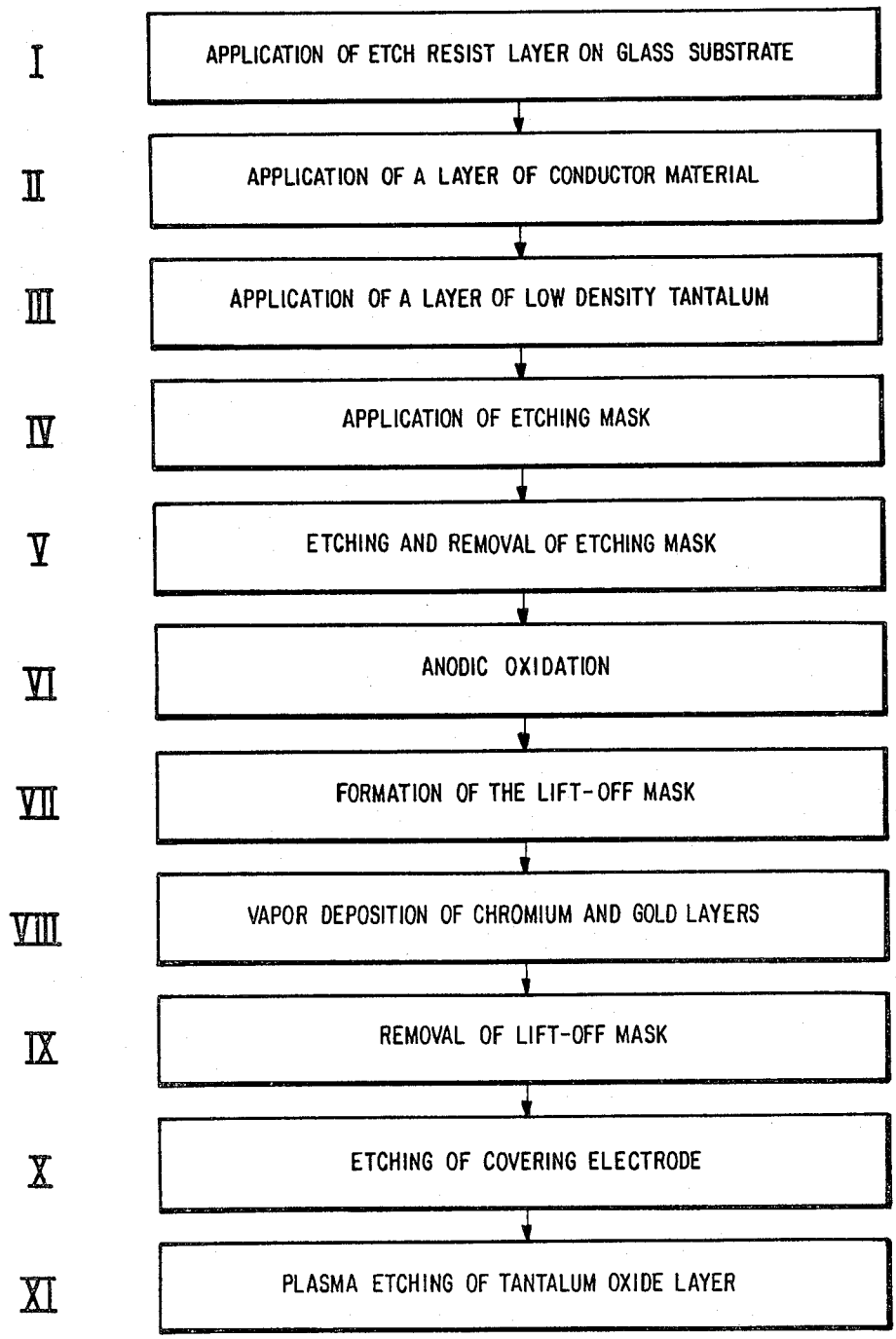

MOISTURE SENSOR WITH VALVE METAL COMPOSITION ELECTRODES

BACKGROUND AND SUMMARY OF THE INVENTION

The invention relates to a moisture sensor comprising a thin layer formed from the oxide of highly resistive porous low density tantalum applied on a moisture-insensitive substrate and at least two electrodes provided at the tantalum oxide layer in spaced-apart relationship, and a method of manufacturing such a moisture sensor.

A moisture sensor of this type is disclosed in commonly assigned U.S. patent application Ser. No. 272,065, filed June 9, 1981, now U.S. Pat. No. 4,433,319. In most of the embodiments of the moisture sensor described in said patent application one of the two electrodes is a base electrode disposed between the substrate and the tantalum oxide layer. Said base electrode in all instances is formed jointly with the tantalum oxide layer by oxidizing a layer of low density tantalum only over part of its thickness so that below the tantalum oxide layer there remains a portion of metallic low density tantalum forming the base electrode. This mode of forming the base electrode is possible with the low density tantalum mentioned in the elder application having a resistivity in the order of up to 40,000 $\mu\Omega cm$. At the density and porosity of the low density tantalum corresponding to this resistance value controlled oxidation down to the desired depth is possible.

However, meanwhile it has become possible by suitable selection of the parameters in sputtering the low density tantalum to reach resistivity values in the order of 1 $\Omega cm$ and more. A low density tantalum of this resistivity is so porous that the depth of oxidation, especially when the latter is effected by anodizing, can no longer be controlled down to a desired depth; rather does the low density tantalum oxidize uniformly and simultaneously throughout the film thickness. The production methods described in the elder application then do not leave a base electrode.

The invention has as its object an improvement of the moisture sensor of the elder application so that it can be provided in a simple way with a base electrode even if the tantalum oxide layer is formed from low density tantalum of extremely high resistivity.

According to the invention this is accomplished in that the base electrode disposed between the substrate and the tantalum oxide layer consists of valve metal of a density higher than the density of the low density tantalum from which the tantalum oxide layer is formed.

As is well known, the term "valve metal" is used for anodically oxidizable metals which include especially tantalum, aluminum, niobium and hafnium. The use of such a metal for the base electrode which metal, however, must have a density higher than that of the low density tantalum layer from which the moisture-sensitive tantalum oxide layer is formed, offers the advantage that with the measures of the method described in the elder application the tantalum oxide layer can be formed by oxidation (especially anodic oxidation) of low density tantalum of extremely high resistivity while the base electrode remains intact. While the oxidation of the extremely high-resistive low density tantalum takes place simultaneously throughout the film thickness, the metal of the base electrode is continuously oxidized proceeding from the surface, the depth of oxidation being determined by the oxidation parameters. In this way the oxidation process can be reliably controlled without the base electrode disappearing. The oxide layer forming from the metal of the base electrode offers the additional advantage that it may act as insulation against the required counter-electrode. Therefore, the counter-electrode may be applied (especially in the form of a covering electrode) directly onto the oxidized structure.

Special advantages are attained when the metal used for the base electrode is also tantalum, yet of a higher density than that of the low density tantalum layer used for the formation of the moisture-sensitive tantalum oxide. Then it is possible to sputter the two layers in substantially a single operation in the same apparatus by merely selecting the sputtering parameters so as to obtain the desired different densities.

Since the moisture-sensitive layer of the moisture sensor of the invention can be made from extraordinarily porous tantalum oxide, it exhibits very high sensitivity.

By way of a further improvement the rate of response of the moisture sensor can be substantially increased if it is provided with a covering electrode partially covering the tantalum oxide layer and having windows through which the water vapor containing medium can penetrate into the moisture-sensitive tantalum oxide layer. Only the regions of the tantalum oxide layer disposed between the electrodes are active in measuring the moisture so that the water vapor must first penetrate through the inactive regions disposed below the windows in order to reach the active regions. According to the invention, the rate of response of the moisture sensor is substantially increased by removal of the inactive regions of the tantalum oxide layer below the windows. Preferably the inactive regions are removed by plasma etching with the use of the covering electrode as etching mask.

Advantageous modifications of the moisture sensor and methods of manufacturing the same are characterized in the subclaims.

Further advantages and features of the moisture sensor according to the invention and of the method of manufacturing the same will be apparent from the following description of an example with reference to the drawings.

BRIEF DESCRIPTION OF THE DRAWINGS

FIG. 1 is a flow diagram of the method steps of a preferred method of manufacturing a moisture sensor;

FIGS. 2a to 2l are sectional views of various stages of manufacture in the course of the production of the moisture sensor according to the method of FIG. 1.

DETAILED DESCRIPTION OF THE PREFERRED EMBODIMENTS OF THE INVENTION

The production of a preferred embodiment of the moisture sensor will now be described with reference to the flow diagram of FIG. 1, the sectional views of FIGS. 2a to 2l, and the plan views of FIGS. 3a to 3e.

Figure 2A:
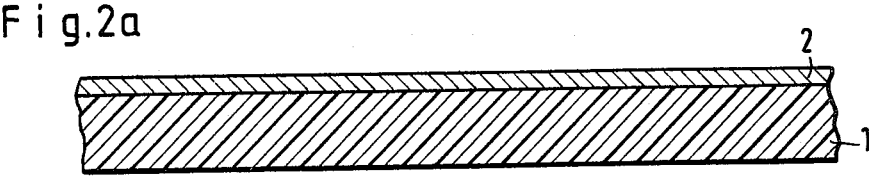
Figure 2B:
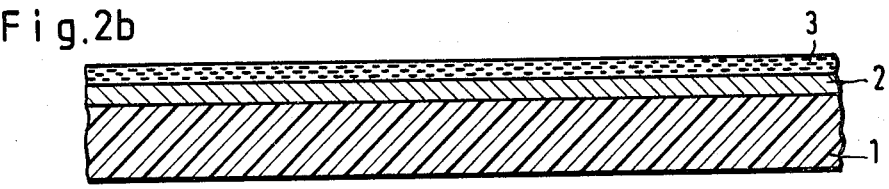

In step I an etch resist layer 2 is applied onto a substrate 1 of glass or another light transmissive material (FIG. 2a). The etch resist layer 2 is required especially when in step V wet chemical etching is effected with hydrofluoric acid, because hydrofluoric acid attacks glass. The etch resist layer 2 may consist of tantalum oxide $Ta_2O_5$ and may be formed by first sputtering in a vacuum onto the glass substrate 1 of a thickness of 0.6 mm, for example, a tantalum layer having a thickness of about 150 nm and thereafter oxidizing said layer. Oxidation may be effected in air at a temperature of about 450° C.; it should last for at least 5 hours, preferably up to about 16 hours. The resulting tantalum oxide layer 10 has a thickness of about 300 nm.

Figure 2C:
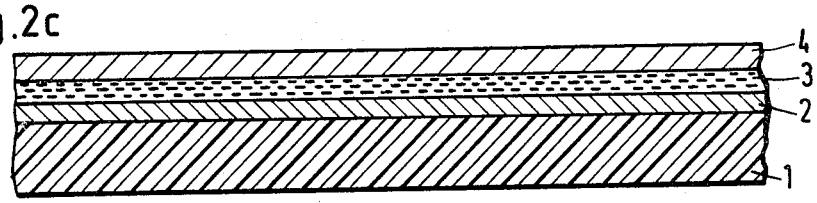

In step II a layer 3 of the conductor material of which later the base electrode of the moisture sensor is to consist (FIG. 2b) is applied on the etch resist layer 2, and thereafter in step III a layer 4 of highly resistive low density tantalum is applied on the layer 3 (FIG. 2c).

It is especially favorable in applying the layers 3 and 4 to make also the layer 3 of tantalum and to apply the two layers 3 and 4 by cathode sputtering. In this way it is possible to apply the two layers in a single operation in the same apparatus with the use of the same starting material; only the parameters are selected differently during sputtering so that the layer 3 is formed from tantalum of a density substantially higher than that of the layer 4.

For example, the layer 3 may consist of solid tantalum of the α- or of the β-modification. Tantalum of the α-modification is known to have a density of 15.6 g/cm³ and a resistivity of 25 to 50 $\mu\Omega$cm, and tantalum of the β-modification has a density of 15.9 g/cm³ and a resistivity of 180 to 220 $\mu\Omega$cm. These values do not materially differ from the properties of bulk tantalum which has a density of 16.6 g/cm³ and a resistivity of 13 $\mu\Omega$cm.

In contrast thereto, low density tantalum is a special modification of tantalum which, like the previously mentioned α- and β-modifications, likewise occurs only in thin layers but differs substantially from the latter and thus also from bulk tantalum regarding its structure, density and resistivity. Low density tantalum is formed under certain conditions when tantalum is sputtered in thin layers; the essential parameter is the sputtering voltage, i.e. the accelerating voltage of the argon ions. With decreasing sputtering voltage the structure of the tantalum in the thin layer becomes increasingly porous, and the density drops accordingly to values as low as 10 g/cm³ and less, while the resistivity assumes very high values. While it is stated in the elder application that values up to 40,000 $\mu\Omega$cm can be attained, it recently has become possible by suitable selection of the sputtering parameters to produce layers from low density tantalum having a resistivity in the order of 1 $\Omega$cm. Such tantalum layers have a highly porous structure and accordingly low density.

It is desirable that in the structure shown in FIG. 2c the layer 4 consists of tantalum having minimal density and accordingly high resistivity so that the tantalum of the layer 4 has a highly porous structure. On the other hand, the layer 3 is to consist of tantalum of a density substantially higher than that of the layer 4. For the reasons explained above these different properties of the layers 3 and 4 can be attained in the course of a single sputtering operation simply by variation of the sputtering parameters. This can be accomplished in various ways:

Initially the sputtering parameters are selected so that the layer 3 is formed of tantalum of the α-modification or the β-modification. As soon as the desired layer thickness is reached the sputtering parameters are changed so that the layer 4 builds up from low density tantalum having minimal density.

The sputtering parameters are initially selected so that the layer 3 forms from low density tantalum still having relatively high density, e.g. of a resistivity in the order of 5000 $\mu\Omega$cm. After the desired layer thickness has been reached the sputtering parameters are so changed that the layer 4 builds up from low density tantalum of substantially lower density, e.g. of a resistivity in the order of 1 $\Omega$cm.

The sputtering parameters are initially selected so that the layer 3 is first formed from low density tantalum of relatively high density, e.g. of a resistivity of 5000 $\mu\Omega$cm. During the formation of the layer 3 the sputtering parameters are varied continuously so that the tantalum density in the layer 3 gradually decreases and the resistivity gradually increases accordingly. After the density and the resistivity have reached the values desirable for the layer 4, the sputtering parameters are no longer varied and the layer 4 is formed in the desired thickness.

For reasons of clarity it will be assumed in the following description that the layers 3 and 4 have been applied according to one of the two first described measures so that a distinct boundary can be discerned between the layers 3 and 4. The thickness of the layers 3 and 4 may be in the order of 100 to 400 nm. In the interest of better understanding the film thicknesses are not shown true to scale in the drawings.

Figure 2D:
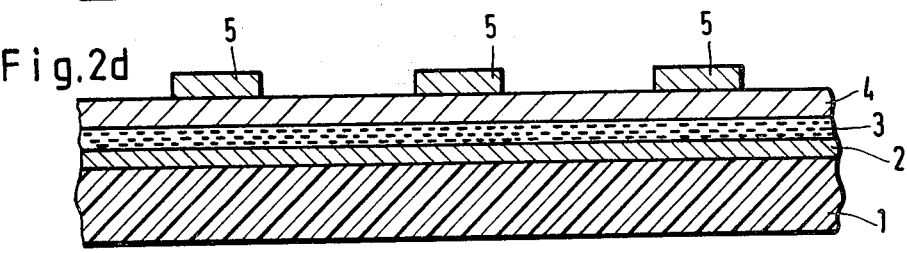

Steps IV and V serve to shape the base electrode and the moisture-sensitive layer. To this end an etching mask 5 is applied on the layer 4 in step IV. This may be done in a conventional manner photolithographically by covering the entire surface with a photoresist film of 2 to 3 $\mu$m thickness, whereafter the photoresist is exposed through a template, developed and cured, and finally the uncured portion of the photoresist is removed (FIG. 2d).

In step V the tantalum of the layers 3 and 4 not covered by the etching mask 5 is removed by wet chemical etching. To this end a mixture of hydrofluoric and nitric acids may be employed which has the following composition:

2 parts concentrated $HNO_3$
1 part 48% HF
1 part water

Figure 2E:
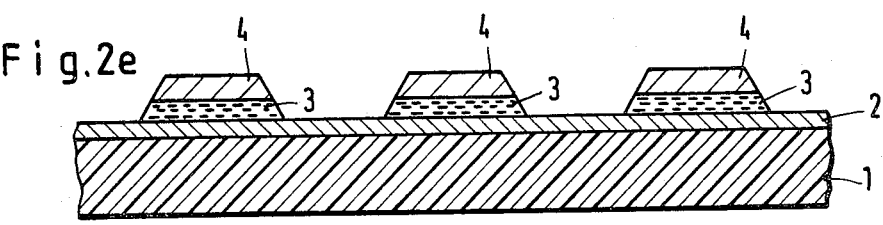
Figure 3A:
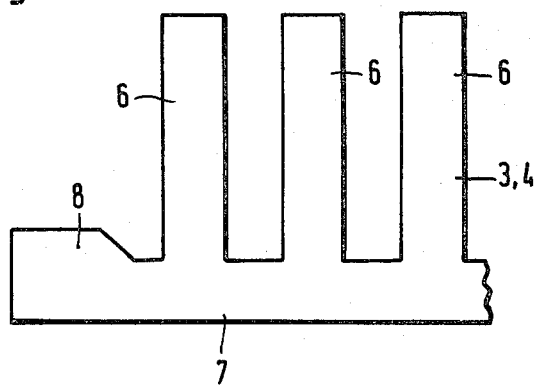
FIGS. 3a to 3e are plan views of the moisture sensor in various stages of manufacture.
Figure 3B:
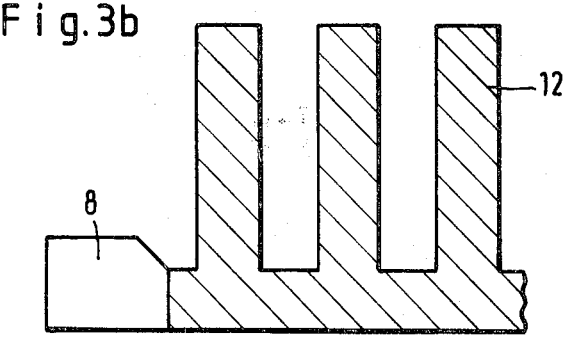

After etching of the layers 3 and 4 and removal of the etching mask 5 there is obtained the structure shown in cross section in FIG. 2e and in plan view in FIG. 3a. It has the configuration of a comb with a multiplicity of parallel teeth 6 connected at one end by a longitudinal web 7. One end of the longitudinal web 7 is enlarged to form a portion 8 which later serves as electrode terminal. For better clarity only a few teeth 6 are shown in FIG. 3a; in reality a multiplicity of teeth is formed to provide maximum possible edge length.

In step VI the moisture-sensitive layer of tantalum oxide $Ta_2O_5$ is formed by anodic oxidation of the highly resistive porous tantalum of the layer 4. Since the electrode terminal 8 must not be oxidized it is covered by an oxidation mask. The oxidation mask can again be formed photolithographically with the use of photoresist in the previously described manner, preferably in a thickness of about 10 to 20 $\mu$m.

Oxidation is accomplished, for example, by anodizing in aqueous electrolyte. For this purpose a 0.01% citric acid may be employed. The tantalum layers 3 and 4 are connected to the positive terminal of the voltage source. After removal of the oxidation mask the structure has the appearance shown in FIGS. 2f and 3b.

Figure 2F:
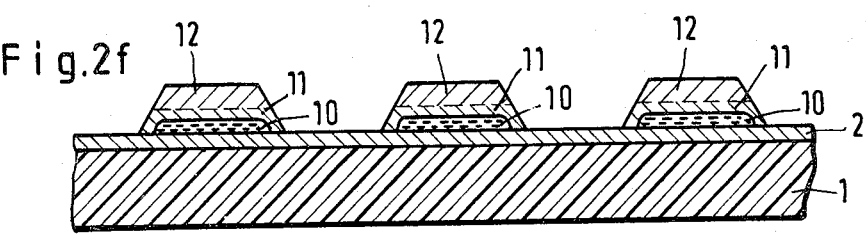

The sectional view of FIG. 2f illustrates that the highly porous and highly resistive tantalum of layer 4 is oxidized throughout, while the denser tantalum of layer 3 is oxidized only to a certain penetration depth so that below the oxide layer there is still metallic tantalum. This is the consequence of the very different densities of the tantalum in the layers 3 and 4. In the highly porous tantalum of the layer 4 oxidation takes place virtually instantaneously throughout the thickness of the layer so that it is not possible to control especially the oxidation depth by the oxidizing conditions. In the substantially denser tantalum of layer 3, on the other hand, oxidation takes place gradually from the outside inwardly, as usual, in dependence upon the current density and the anodizing voltage so that the oxidation depth can be controlled by adjustment of these values.

The resulting structure thus contains a comb-shaped metallic base electrode 10 consisting of the remaining metallic tantalum of the layer 3 which is electrically connected to the electrode terminal 8 wherein the metallic tantalum of the original layers 3 and 4 is still preserved. The base electrode 10 is covered with a tantalum oxide layer 11 formed by anodic oxidation of the denser tantalum of the layer 3. On top of the tantalum oxide layer 11 there is a tantalum oxide layer 12 formed by complete anodic oxidation of the low density tantalum of layer 4. The tantalum oxide layer 12 constitutes the moisture-sensitive layer proper of the moisture sensor. Since the tantalum of the layer 4 was extraordinarily porous, the tantalum oxide layer 12, too, has a highly porous structure with the consequence that it is particularly moisture-sensitive and, in response to the absorbed moisture, the dielectric constant as well as the resistivity are subject to considerable change. Nevertheless, the electric long-term stability and chemical resistance of this porous tantalum oxide is equal to that of normal tantalum oxide.

Steps VII to IX of the method serve to form the covering electrode according to the so-called "lift-off" technique with the use of a previously applied mask.

Figure 2G:
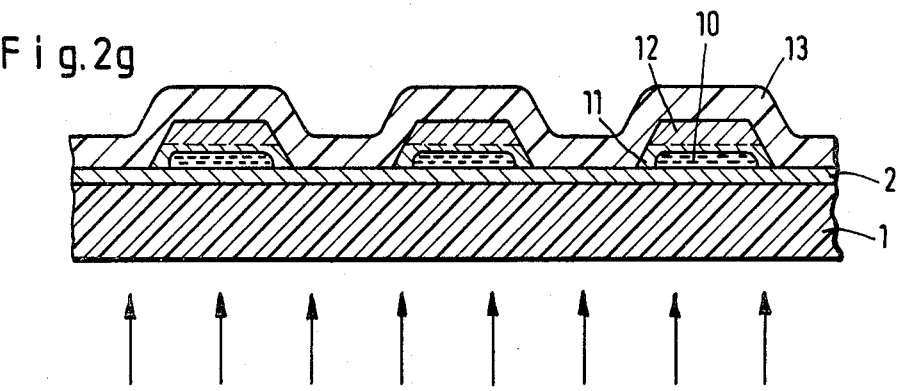
Figure 2H:
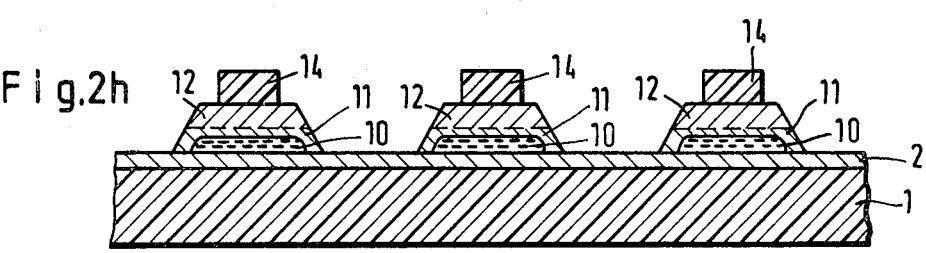
Figure 3C:
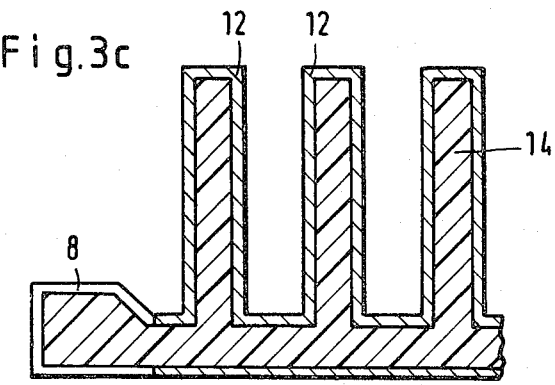
Figure 3D:
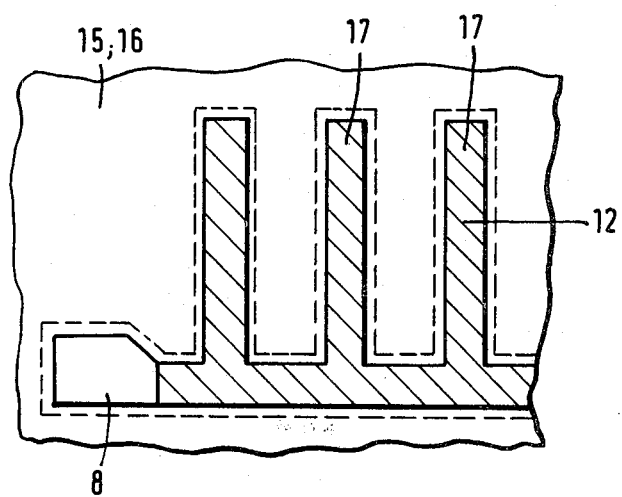

In step VII the "lift-off" mask is formed. To this end the last formed comb structure (FIGS. 2f and 3b) is covered with a photoresist film 13 which is then exposed to light through the glass substrate 1 (FIG. 2g). In this process the previously obtained comb structure composed of the base electrode 10 and the oxide layers 11 and 12 functions as exposure mask. After development of the photoresist layer 13 the exposed portions are removed leaving only the unexposed portions as "lift-off" mask 14 (FIGS. 2h and 3c). The "lift-off" mask 14 has the configuration of the comb structure and covers the oxide layer 12 with the exception of a narrow region along the edges. The somewhat lesser width of the "lift-off" mask 14 is the consequence of scattering of light along the edges of the comb structure serving as exposure mask.

Figure 2I:
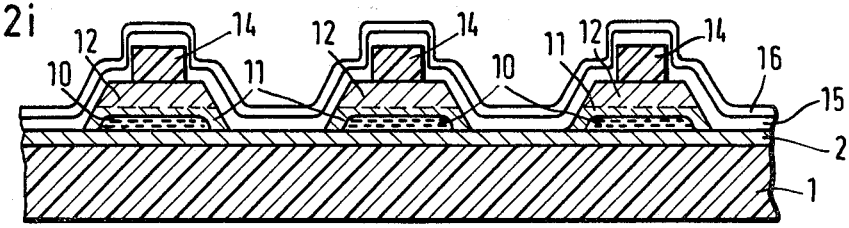

In step VIII the metal layers which are later to form the covering electrode are vapor deposited over the entire surface area of the last obtained structure. Gold is preferably used as conductor material for the covering electrode. However, since gold adheres poorly to tantalum oxide, a chromium layer 15 is first vapor deposited over the entire surface area and thereafter covered with a gold layer 16 applied by vapor deposition (FIG. 2i). In lieu of chromium also titanium or tantalum may be used to form the bonding layer. When tantalum is used as bonding layer it is advisable to interpose a chromium layer between the tantalum layer and the gold layer. The topmost layer of the covering electrode may also consist of aluminum in lieu of gold.

In step IX the "lift-off" mask of photoresist together with the overlying chromium and gold is dissolved away. The solvent (acetone) penetrates through the chromium and gold along the thinly covered edges of the photoresist mask. The resulting structure is shown in section in FIG. 2k and in plan view in FIG. 3d. The dissolution of the "lift-off" mask leaves a comb-shaped window 17 exposing the tantalum oxide layer 12. Since the chromium and gold layers 15, 16 still cover the entire remaining surface area of the substrate, the portions not required are removed by a following etching operation in step X to impart the final configuration to the covering electrode 18 shown in FIG. 3e in plan view. Etching may be effected in the same way as previously explained for the formation of the base electrode 10 in method steps IV and V by first forming an etching mask by exposure and development of a photoresist layer, then removing the chromium and gold layers by wet chemical etching in the areas not covered by the etching mask, and finally removing the etching mask. Of course, etching agents must be used which are suitable for chromium and gold; suitable examples are given in the elder application.

Figure 2K:
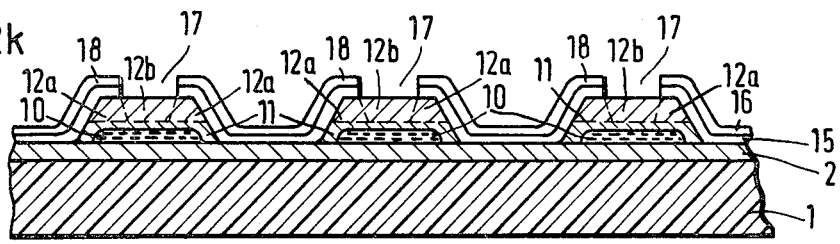

The sectional view of FIG. 2k shows that the covering electrode 18 is completely separated from the base electrode 10 by the tantalum oxide layers 11 and 12. Along the edges it somewhat overlaps the top side of the moisture-sensitive tantalum oxide layer 12 which otherwise is exposed in the areas formed by the window 17. Consequently there is a certain degree of mutual overlapping between the base electrode 10 and the covering electrode 18 which is advantageous to the sensitivity of the moisture sensor because the active moisture sensing portion of the tantalum oxide layer 12 is formed by the regions disposed between the electrodes 10 and 18 designated 12a in FIG. 2k.

Of course, the covering electrode 18 can be formed also in other ways. Thus, for example, the window 17 could be formed also along with the shaping of the covering electrode in step X of the method, so that steps VIII and IX would become unnecessary. The described "lift-off" method including the formation of the "lift-off" mask by "back exposure" through the glass substrate 1 offers essential advantages:

Since the comb structure of the base electrode itself forms the exposure mask, it is unnecessary to provide a special exposure mask which would have to be precisely positioned. It has to be borne in mind that the precision requirements in the formation of the comb structure of the covering electrode are substantially more rigid than those in the formation of the external contour. The method employed permits self-adjustment of the position of the covering electrode relative to the position of the base electrode and of the oxide layers.

The desired degree of mutual overlapping of base electrode and covering electrode is controllable by the duration of the back exposure. The longer the exposure period, the higher will be the degree of overlapping.

Figure 3E:
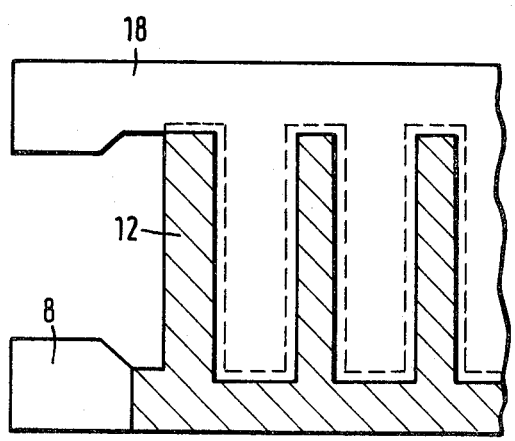

The assembly illustrated in FIGS. 2k and 3e already forms an operable moisture sensor. However, by additional shaping in step XI the speed of response of the moisture sensor is significantly increased.

The speed of response of the moisture sensor is determined by the time it takes the water vapor to get to the active regions 12a (FIG. 2k). It first must penetrate through the inactive regions 12b disposed below the areas formed by the window 17.

By etching the inactive regions 12b of the tantalum oxide layer 12 away in step XI the response time of the moisture sensor is greatly reduced. A suitable etching method is plasma etching in $CF_4$ with an addition of $O_2$. If the topmost layer of the covering electrode 18 consists of gold or aluminum, the covering electrode 18 itself may be used as etching mask because these metals exhibit a very low etching rate in the above mentioned plasma. In that case no special etching mask is required.

Figure 2L:
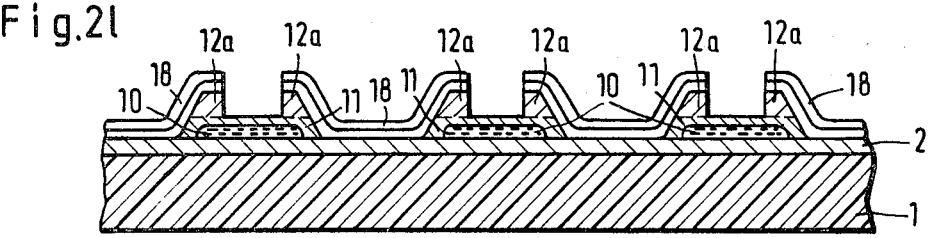

After completed etching the final moisture sensor has the structure shown in FIG. 2l. The water vapor can penetrate directly into the active regions 12a of the tantalum oxide layer 12. With a moisture sensor formed in this way it was possible to reach the 95% value of the moisture sensor output signal upon a moisture jump from 5 to 95% relative humidity in less than 1 second.

In the above described production method various intermediate or after-treatments can be performed, of course, between individual method steps and at the end in order to improve the properties of the moisture sensor. Examples for such intermediate and after-treatments are given in the elder application. Cleaning of the tantalum oxide layer surface by sputter etching and annealing at a temperature of up to 400° C. has proved to be especially favorable.

Of course, the invention is not limited to the previously described example. Various modifications thereof will be apparent to an expert.

In particular, the material for the base electrode 10 may be an anodically oxidable metal other than tantalum, especially aluminum, niobium or hafnium. Such metals are known by the term "valve metals".

The use of a base electrode made from a metal having a density higher than that of low density tantalum whose oxide forms the moisture-sensitive layer is possible also for other structures of the moisture sensor, e.g. in all the structures described in the elder application. This measure is independent of the type, shape and production of the counter-electrode.

An increase of the speed of response by etching away the inactive regions of the moisture-sensitive tantalum oxide layer is possible in all moisture sensors having a covering electrode provided with cut-out portions or windows through which the water vapor can penetrate into the moisture-sensitive layer.

What we claim is:

1. A moisture sensor comprising a thin layer of the oxide of highly resistive porous low density tantalum on a moisture-insensitive substrate and at least one base electrode disposed between the substrate and said tantalum oxide layer, wherein the base electrode disposed between the substrate and said tantalum oxide layer comprises a thin layer of valve metal of a density higher than the density of the highly resistive low density tantalum from which said tantalum oxide layer has been formed.

2. Moisture sensor according to claim 1 wherein the base electrode consists of tantalum.

3. Moisture sensor according to claim 2 wherein the electrode is formed of a thin layer that is selected from the group consisting of tantalum of the α- and β-modification applied on the substrate.

4. Moisture sensor according to claim 2 wherein the base electrode is formed of a thin layer of low density tantalum having a density substantially higher than the density of the low density tantalum of which the moisture-sensitive tantalum oxide layer is formed.

5. Moisture sensor according to claim 4 wherein the density of the low density tantalum forming the base electrode continuously decreases from the substrate toward the tantalum oxide layer.

6. Moisture sensor according to claim 1 wherein the base electrode consists of aluminum.

7. Moisture sensor according to claim 1 wherein the base electrode is selected from the group consisting of niobium and hafnium.

8. Moisture sensor according to claim 1 wherein the metal of the base electrode is oxidized through part of its thickness.

9. Moisture sensor according to claim 1 comprising a covering electrode partially covering the tantalum oxide layer and having windows through which the water vapor containing medium can penetrate into the moisture-sensitive tantalum oxide layer, the inactive regions of the tantalum oxide layer disposed below the said windows being removed.

10. Moisture sensor according to claim 9 wherein the inactive regions of the tantalum oxide layer have been removed by plasma etching.

11. Moisture sensor according to claim 9 wherein the base electrode and the covering electrode are in overlapping relationship with the tantalum oxide layer interposed therebetween.

12. Moisture sensor according to claim 1 wherein the structure formed by the base electrode and the tantalum oxide layer covering same has the shape of a first comb with teeth joined at one end by a web, and the covering electrode has the shape of a second comb whose teeth overlap the interstices between the teeth of the first comb and the marginal regions of the teeth of the first comb.

* * * * *